United States Patent [19]

Shishido

[11] Patent Number: 4,793,326

[45] Date of Patent: Dec. 27, 1988

[54] ENDOSCOPE HAVING INSERTION END GUIDE MEANS

[75] Inventor: Yoshio Shishido, Sagamihara, Japan

[73] Assignee: Olympus Optical Co., Ltd., Tokyo, Japan

[21] Appl. No.: 127,070

[22] Filed: Dec. 1, 1987

[30] Foreign Application Priority Data

Dec. 8, 1986 [JP] Japan .................. 61-292779
Feb. 19, 1987 [JP] Japan .................. 62-34459
Feb. 19, 1987 [JP] Japan .................. 62-22065[U]

[51] Int. Cl.⁴ .............................. A61B 1/00
[52] U.S. Cl. .......................... 128/4; 356/241
[58] Field of Search .............. 128/4, 6; 356/241

[56] References Cited

U.S. PATENT DOCUMENTS 3,960,143  6/1976  Terada .................. 128/4
4,676,229  6/1987  Krasnicki et al. ........ 128/4

FOREIGN PATENT DOCUMENTS 59-143401  9/1984  Japan .

Primary Examiner—William H. Grieb
Attorney, Agent, or Firm—Ladas & Parry

[57] ABSTRACT

An endoscope is disclosed which comprises an elongated insertion section and operation section, connected to one end thereof and which controls the insertion section from outside of a pipe structure. The insertion section includes an elongated flexible section, and an angle section connected thereto. The degree of curvature of the angle section is controlled by the operation section. The insertion section also includes a rigid section which is connected to the distal end of the angle section, and which incorporates an observation window which permits observation of the inner wall of the pipe structure. A guide means is attached to the rigid section, in order to guide the rigid section smoothly around a curve or bend in the pipe structure. The guide means has an elongated arm member which extends substantially along the axial direction of the rigid section and has a structural flexibility appropriate to ensure its smooth passage through the interior of the pipe structure. The first end of the arm member is fixed to the rigid section, and its other end is fixed to a slide member which slides along the inner surface of the pipe structure.

23 Claims, 8 Drawing Sheets

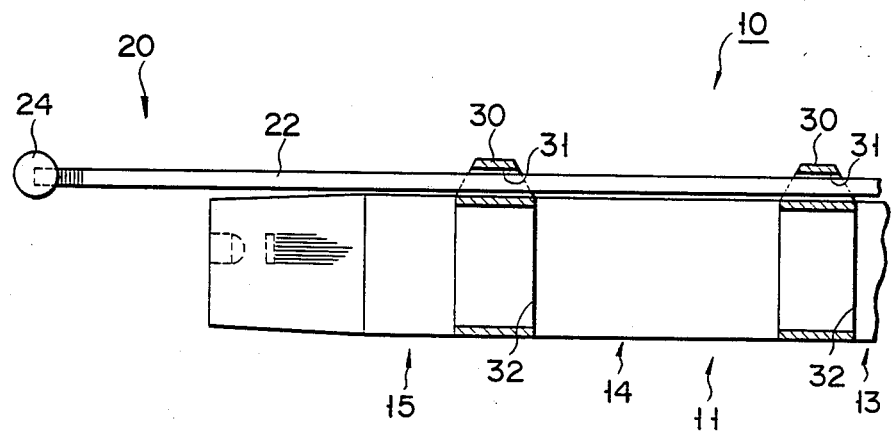
F I G. 14
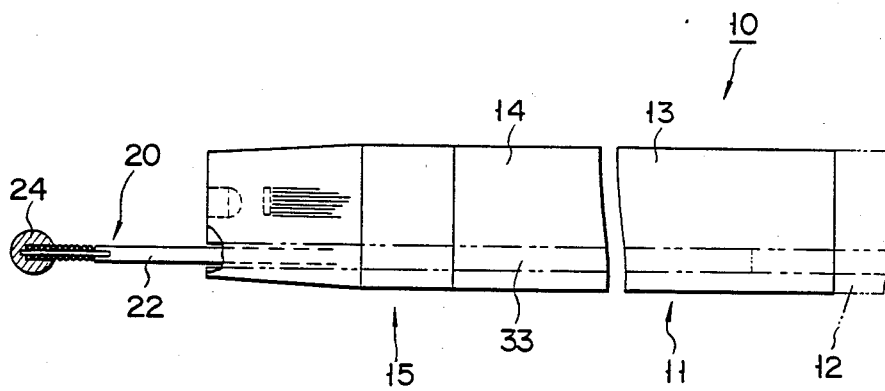
F I G. 15
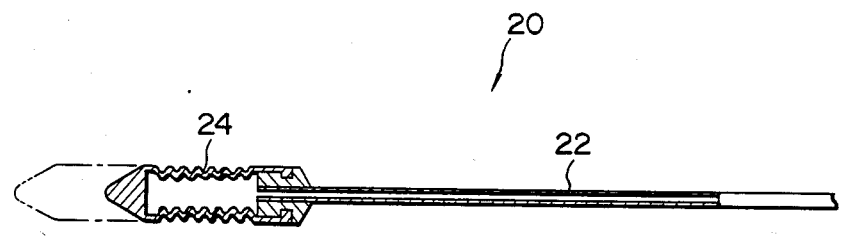
F I G. 16

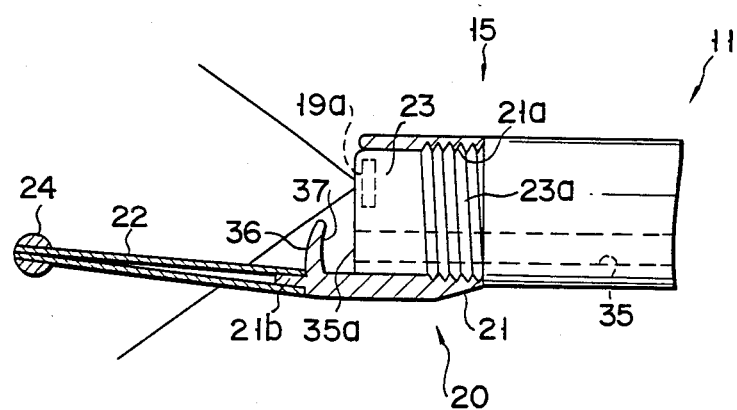
F I G. 19
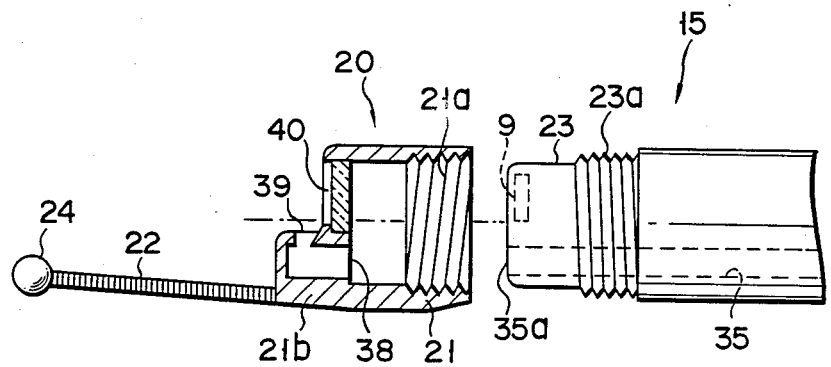
F I G. 20
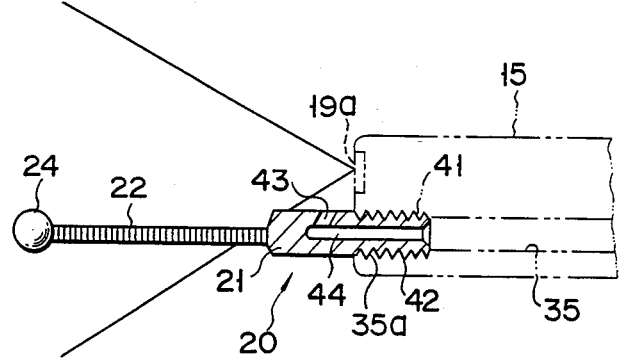
F I G. 21

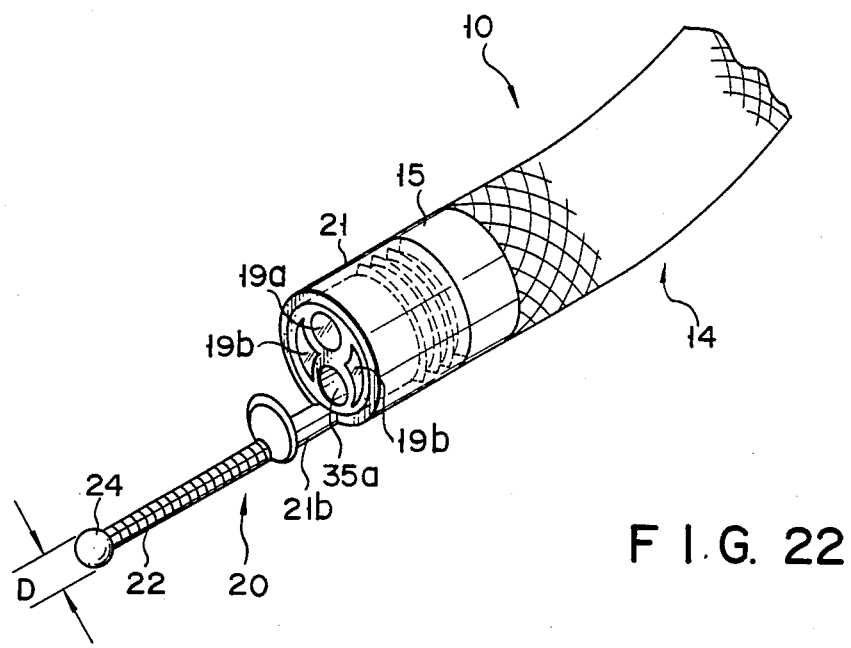
F I G. 22
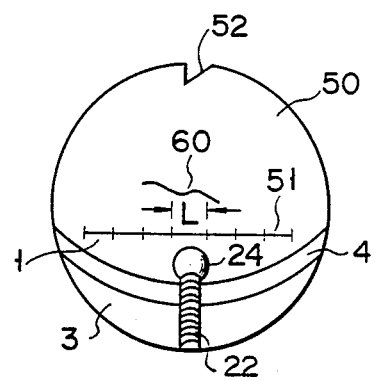
F I G. 23
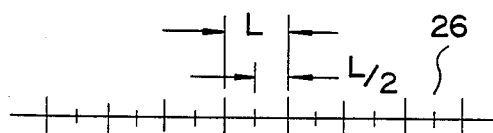
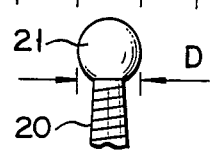
F I G. 24

ENDOSCOPE HAVING INSERTION END GUIDE MEANS

BACKGROUND OF THE INVENTION

This invention relates to an endoscope having a section which can be inserted into a channel and, in particular, into a bent channel.

An endoscope which can be used to observe the inner surface of a bent channel, such as a water supply pipe or gas pipe, is known. Such an endoscope is generally referred to as an industrial endoscope and is a very effective and efficient means for observing the inner surfaces of, for example, a complex machine or a narrow tube.

As is shown in FIGS. 1 and 2, straight tubes 1 and 2 are jointed by elbow 3, with abrupt step 4 being formed between the straight tubes and the elbow. When the distal end of endoscope 5 is to be inserted to permit observation of the inner surface of the curved section of elbow 3, angle section 6 of endoscope 5 is bent, by means of an external operation, at abrupt step 4, so as to prevent it from abutting thereagainst. In this way, the end face of distal end 5 of the endoscope is oriented inwardly away from abrupt step 4, after which the distal end of the endoscope is pushed further into the channel of the tube.

In this case, if abrupt step 4 at the location of the elbow is pronounced, the possibility is increased that angle section 6 of the endoscope will become jammed against step 4 upon being moved along the inner surface of elbow 3. If jamming occurs, attempts to force the insertion section further into the tube will most likely result in damage to the angle section. Therefore, the insertion section must be partially withdrawn each time an obstacle is encountered and attempts are made to guide it away from the obstacle, so as for it to be inserted further into the tube. This makes usual inspection of the interior of the tube a more time-consuming proper than is desirable. Moreover, after the distal end of endoscope 5 has successfully negotiated, for example, three or more curves or bends, it becomes less likely, from a structural point of view, that angle section 6 of the endoscope will then be able to continue to bend sufficiently to be able to negotiate further bends or curves. As a result, distal end 7 of the endoscope becomes jammed against an obstruction, at which point it is no longer possible to continue observation of the interior of the tube.

Thus, where a tube comprises three or more abrupt bends or curves, the conventional endoscope ceases to be an efficient means of observing the interior of such a tube.

Japanese Patent Disclosure (KOKAI) No. 59-143401 discloses an industrial endoscope which permits clear observation of the interior of a tube by washing away any foreign matter coated on the inner surface of an observation window.

In this type of endoscope, opposite to the observation window provided at the face end of a rigid portion of the endoscope an outlet for injecting a washing liquid is formed at a hood attached to the rigid section of the endoscope or a washing liquid injecting nozzle is formed such that it is opened at the end face of distal-side rigid section of the endoscope.

This endoscope can effectively be used to observe the interior of the tube which is readily liable to be deposited with a dirty or rusty substance. This type of endoscope, however, never has any angle section and, if it has, poses such a problem as set forth above.

Japanese Patent Disclosure (KOKAI) No. 56-158631 discloses an industrial endoscope having a graduation mark within a visual field which is obtained through an eyepiece section.

This endoscope can precisely determine the size, etc., of a defect, such as a damaged spot, or a rusty spot on the inner wall of the tube and is very useful to observe the interior of the tube.

In order for the dimensions of a given part or spot to be accurately measured by means of the graduation, it is necessary that a predetermined distance be maintained between the distal end rigid section and, in particular, an observation window and a spot to be measured. For the exact determination of that distance for measurement, an optically, fairly complex structure results. In this case, the aforementioned problems occur when the distal end of the endoscope is inserted into a complicatedly bent tube, to observe its inner surface.

SUMMARY OF THE INVENTION

It is accordingly the object of this invention to provide an industrial endoscope of a simpler structure which permits clear observation of the inner wall of a complicatedly bent tube structure.

According to this invention, an endoscope is provided which comprises:

an elongated insertion section which can be inserted into a tube structure;

an operation section which is connected to a base end of the insertion section, and which controls the insertion section from outside of the tube structure;

the operation section including an eyepiece section located thereon, and the insertion section including a flexible section, connected at its base end to the operation section, an angle section, connected at its base end to the remote end of the flexible section and its curvature being controlled by the operation section, and a rigid section, connected at its base end to the remote end of the angle section and having an observation window which enables observation of an inner wall of the tube structure; and guide means mounted on the rigid section, for guiding rigid section along an inner wall of the tube structure and around any curve or bend thereof, wherein the guide means includes an elongated arm member extending substantially in the axial direction of the rigid section and having a structural flescibility appropriate to ensure its smooth passage through the interior of a tube structure, the first end of the arm member being fixed to the rigid section, and the guide means further includes a slide member which is fixed to the second end of the arm member and is slidable along the inner surface of the tube structure.

In the case of the present invention, the guide means mounted on the rigid section can be regarded as being, in effect an extension of the rigid section. The rigid section can negotiate a bend or curve at a joint section of a channel simply by bending the angle section. This rigid section can successfully pass through a number of curves or bends without the angle section losing its ability to bend or curve. Through the presence of the slide member and the arm member, the rigid section, that is, the insertion section of the endoscope, can be guided positively and smoothly through the tube structure without becoming jammed at a bend or curve thereof. In this way, a complicatedly curved or bent tube structure can be observed in an efficient and effective manner.

BRIEF DESCRIPTION OF THE DRAWINGS

FIGS. 11 to 33 are explanatory views showing portions of guide means of seventh to ninth variants of the first embodiment, according to which a deposit on the inner wall of a tube can be picked up;

FIGS. 14 and 15 are side views diagrammatically showing respective portions of tenth and eleventh variants of the first embodiment;

FIG. 16 is a cross-sectional view showing a portion of a guide means of a twelfth variant of the first embodiment;

FIG. 17 is a view showing an endoscope, with a portion eliminated, according to a second embodiment of this invention;

FIG. 18 is a perspective view, partly enlarged, diagrammatically showing a portion of the endoscope of FIG. 17;

FIG. 19 is a cross-sectional view, partly enlarged, showing the endoscope of FIG. 17;

FIGS. 20 and 21 are cross-sectional views showing first and second variants of the endoscope of the second embodiment;

FIG. 22 is a perspective view, partly enlarged, showing a portion of the endoscope according to a third embodiment;

FIG. 23 is an explanatory view diagrammatically showing the state of a visual field as obtained through an eyepiece section of the third embodiment; and FIG. 24 is a view, similar to that of FIG. 23, showing a variant of the third embodiment.

DETAILED DESCRIPTION OF THE PREFERRED EMBODIMENTS

Figure 1:
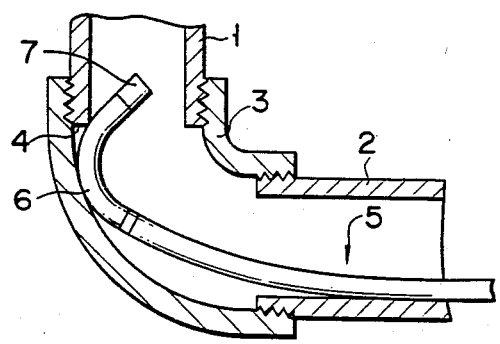
FIGS. 1 and 2 each are an explanatory view showing the inner state of a bend or elbow section under the observation of a conventional endoscope.
Figure 2:
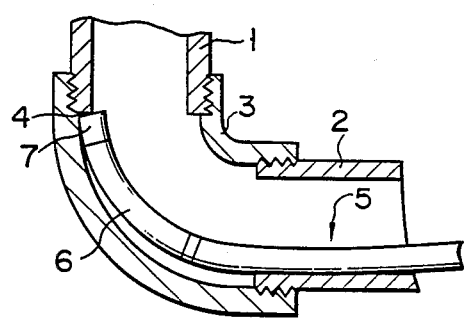
Figure 3:
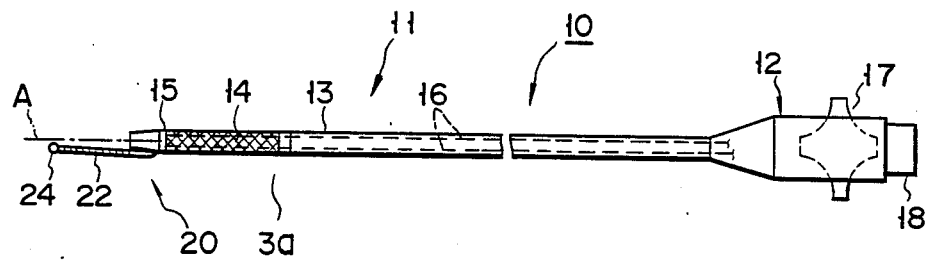
FIG. 3 is a general view diagrammatically showing an endoscope according to a first embodiment of this invention.

FIG. 3 is a side view showing industrial endoscope 10 according to a first embodiment of this invention. Endoscope 10 includes insertion section 11 having such a configuration as to allow it to be inserted into a hollow pipe or a narrow channel space of a complex machine and equipment. Endoscope 10 includes operation section 12 coupled to one end of insertion section 11 and capable of operating the insertion section from outside of the pipe, etc. Insertion section 11 includes narrow flexible section 13 connected to operation section 12, angle section 14 coupled to that end of flexible section 13 remote from operation section 12, and rigid section 15 connected as a distal end to the angle section.

As in the case of the conventional endoscope, angle section 14 is comprised of a greater number of mutually connected rings arranged along their axial direction and a flexible covering, such as a rubber tube and outer metal, fitted on the outer periphery of that ring array. The angle section can properly be bent by pulling operation wire 16 extending up to operation section 12 through the flexible section 13. Stated in more detail, pull wire 16 can be pulled by turning angle operation knob 17 which is provided at operation section 12.

Figure 4:
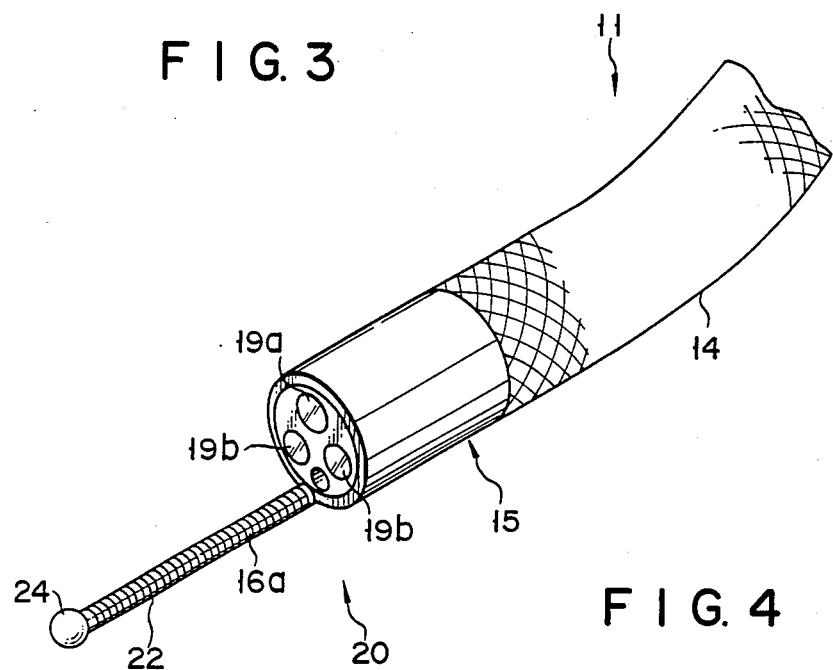
FIG. 4 is a perspective view, partly enlarged, showing the endoscope of FIG. 3.

As shown in more detail in FIG. 4, rigid section 15 has, as with an ordinary endoscope, observation window 19a and illumination windows 19b provided at its distal end face with the observation window constituting a portion of an observation optical system and the illumination window constituting a portion of an illumination optical system. A light beam is emitted from a light source device so that it can be directed to a region of interest (ROI) through a light guide. A light image which is reflected from the inner wall of a pipe, etc., is picked up through observation window 19a and conducted past a light transmitting means, such as an optical fiber, to eyepiece 18 provided at the operation section.

Guide means 20 is attached to rigid section 15, noting that, within the visual field of the operator, the guide means can be viewed, through eyepiece section 18, as extending upwardly from below. Guide means 20 is comprised of arm member 22 extending, from the undersurface of rigid section 15, substantially in the axial direction of guide means 20 (FIG. 3) and bulb-like slide member 24 attached to arm member 22. Bulb-like slide member 24 may not have any step relative to arm member in which case it may be so rounded as to have a near spherical distal end.

Arm member 22 is comprised of a flexible, closely spiral metal coil and has an elasticity and rigidity adequate enough to guide the insertion section of the endoscope. The base end of arm member 22 is integrally jointed by, for example, welding to the under-side of the outer periphery of rigid section 15 of the endoscope and the free end of arm member 22 extends in the axial direction A (FIG. 3) from the underside of the outer periphery of rigid section 15 such that it extends in parallel fashion to the axial direction A or the axial direction A with a slight angle. Slide member 24 is formed integral with the free end of arm member 22 and has a metal ball, or an engineering plastics ball, of excellent friction resistance. The guide means thus provided is formed integral with rigid section 15 of the endoscope and, together with rigid section 15, can be moved by the bending operation of angle section 14.

The arm member 22 of guide means 20 has a length enough adequate to guide rigid section 15 in accordance with the curvature of the bend of the channel structure, or the size of the associated pipe, into which rigid section 15 is guided. Various kinds of arm members are prepared, as required. In order for the operator to recognize the distance of the arm member relative to the inner wall of the channel or associated pipe without his or her visual field's being prevented thereby, it is preferable that slide member 24 be located more on an outer peripheral side than at the middle level of the visual field of the endoscope. The position of slide member 24 within the visual field can properly controlled by adjusting the angle o the guide member relative to the axis A (FIG. 3) in accordance with the length of arm 20, or simply adjusting the length of guide means 20, thus assuring an effective observation. By giving color, as distinct from the color of the ROI, to slide member 24, the slide member serves as a device for measuring the size, distance, etc.

How to observe the inner wall of the bend by the endoscope of this embodiment will be explained below.

Figure 5:
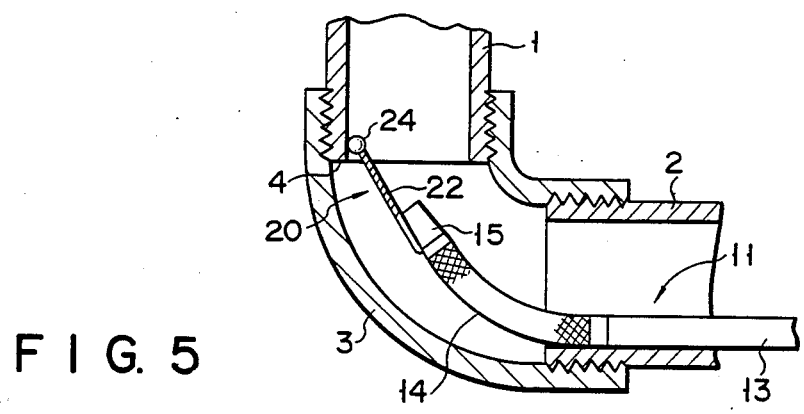
FIG. 5 is a cross-sectional view diagrammatically showing the state of the distal end of the endoscope when the distal end is successfully traversed along the bend.

As shown in FIG. 5, insertion section 11 of the endoscope is inserted into the interior of pipe 2 through the illumination of it with illumination light via the illumination window at the distal end face of rigid section 15 and further inserted into the pipe through the observation of a light image incident via the observation window at the distal end face of rigid section 15.

When rigid section 15 reaches a curved section at elbow 3 by which pipe 2 is connected to pipe 1, the operation knob (17 in FIG. 3) of the operation section is operated at the location of the entry side of the elbow so as to curve angle section 14 along the direction of the curve of elbow 3. Then insertion section 11 of the endoscope is pushed into the pipe, while controlling the curvature of angle section 14, until slide member 24 of guide means 20 abuts against the inner surface of pipe 1 past step 4 defined between elbow 3 and pipe 1. After slide member 24 has abutted against the inner surface of pipe 1, the insertion section of the endoscope is pushed further into pipe 1, while slide member 24 is slidably moved along the inner surface of pipe 1. Since, at this time, slide member 24 is put within the visual field of the operator, the operator can readily recognize the distance of the slide member relative to the inner wall of pipe 1.

Since arm member 22 of the guide means has proper rigidity and elasticity, guide means 20 can smoothly guide rigid section 15 and thus angle section 14 of the endoscope without being latched to the inner surface of elbow 3 or step 4. Furthermore, the guide means, upon being applied by an excessive force, can absorb it.

After angle section 14 has successfully been inserted past the curve or bend into pipe 1, it is so controlled by the operation of the operation knob that angle section 14 extends in a straight direction. Through the further pushing of insertion section 11 the rigid section can be guided up to the ROI in which case the flexible section of the endoscope is not latched to step 4 because it is not bent at a curvature as small as that of angle section 14.

Furthermore, guide means 20, even if reaching the next bend or curve, can successfully traverse that bend by the same operation as set forth above.

Since the guide means can smoothly traverse the step at the bend or curve by a simple bending operation with a proper distance kept, the operator can examine the ROI effectively for a brief period of time by a simple operation.

FIGS. 6 to 16 show the variants of the first embodiment of this invention in which like reference numerals are employed to designate like parts or elements through these Figures.

Figure 6:
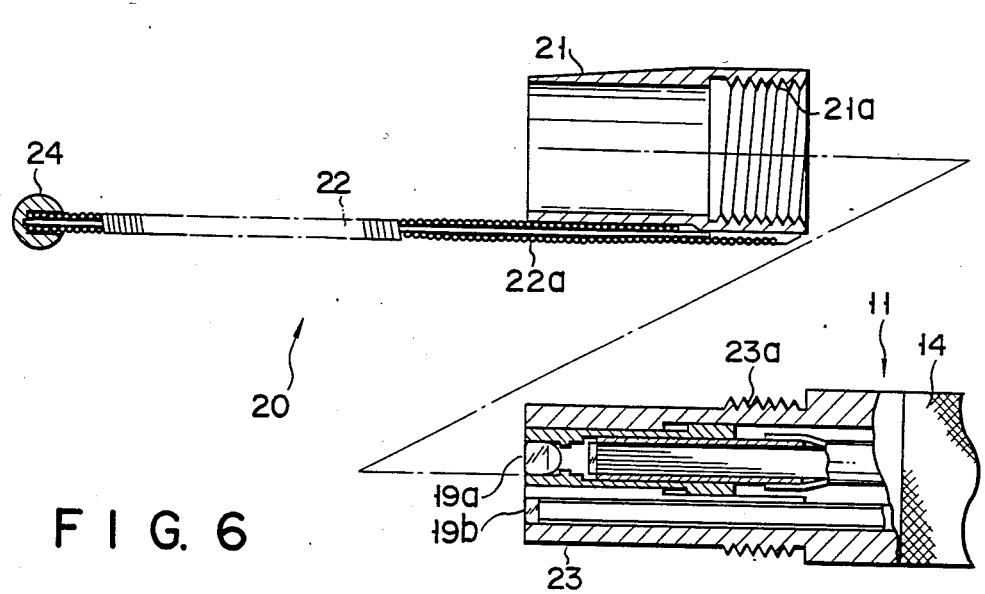
FIG. 6 is a cross-sectional view showing a portion of a first variant of the first embodiment of FIG. 3.

In the first variant shown in FIG. 6, guide means 20 can be detachably mounted relative to rigid section 15.

In the first variant shown in FIG. 6, rigid section 15 through which image and light guides extend is formed as a stepped cylinder, noting that the image and light guides are optically coupled to observation window 19a and illumination window 19b, respectively. External threaded section 23a is formed at least partially on small-diameter distal end section 23 of rigid section 15.

Guide means 20 is comprised of tubular attaching member 21 attached to small-diameter section 23 of rigid section 15, arm member 22 brazed at its base end to attaching member 21 and slide member 24 firmly threaded, or jointed to, on the free end portion of the arm member. Attaching member 21 has internal threaded section 21a inserted over external threaded section 23a of small-diameter section 23 of the rigid section. As in the first embodiment shown in FIGS. 3 and 4, arm member 22 is formed of a flexible, closely spiral metal coil and reinforcing wire 22a is inserted into the flexible metal coil to provide added rigidity.

When guide means 20 is threadably inserted over small-diameter section 23 of the rigid section, slide member 24 of guide means 20 enters within the visual field of the operator. A proper positioning means may be provided between rigid section 15 and attaching member 21 so that, when slide member 24 is re-attached to arm member 22, it can always assume the same position. Furthermore, attaching member 21 and rigid section 15 may be attached to each other by a proper means, such as a snap-fastening means, so long as they are firmly coupled to each other.

In the first variant, guide means 20 may be detached from the rest of the endoscope when the operator wishes to examine the interior of a channel space having no curve or bend. Various types of adaptors, not shown, may be attached to external threaded section 23a of small-diameter section 23, as required.

Figure 7:
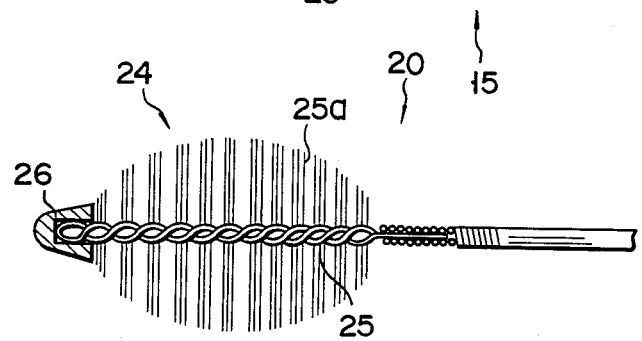
FIG. 7 is an explanatory view, partly in cross-section, showing a portion of a second variant.

FIG. 7 shows guide means 20 of a second variant.

In the second variant, guide means 20 includes a brush as slide member 24. The brush is comprised of core member 25 of a pair of spiral lines coupled to arm member 22 of a flexible coil, wire member 25a fixed to the core member, and cap 26 fixed to the free end of the core member, and is formed as an ellipsoid of revolution.

The second variant can clean the inner wall of a tube member and prevent dust from impeding the observation and illumination optical system.

Figure 8:
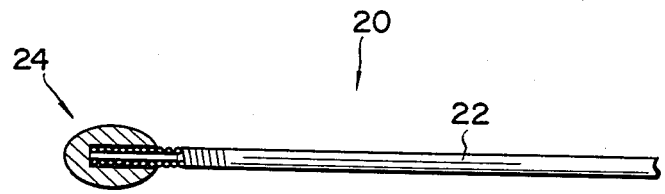
FIGS. 8 to 10 are views, similar to the view of FIG. 7, showing third to sixth variants of the first embodiment of FIG. 3.

In a third variant shown in FIG. 8, guide means 20 is substantially similar to that of the first variant and slide member 24 is formed substantially as an ellipsoid of revolution. Furthermore, slide member 24 may be formed a having a proper shape, such as a spindle, so long as it is not latched to the inner wall of the channel space during the sliding of the slide member along that inner wall FIG. 9 shows guide means 20 of a fourth variant.

Figure 9:
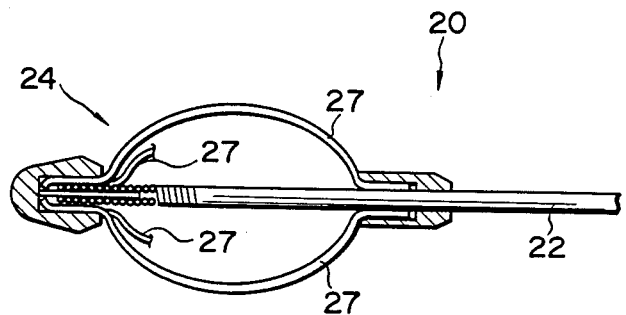

In the fourth variant shown in FIG. 9, guide means 20 is of such a type that a greater number of short wires 27 are externally curved around the free end portion of arm member 22 to provide a spherical shape or ellipsoid of revolution. Both ends of wires 27 are fixed to arm member 22 by a holding means. It is also possible to remove a dust remover or obstruction with it trapped with wires 27.

Figure 10:
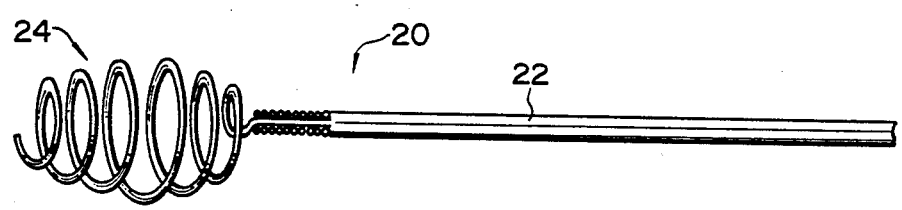

FIG. 10 shows guide means 20 of a fifth variant. Slide member 24 of guide means 20 is formed of a spiral coil having an ellipsoid of revolution.

Figure 11:
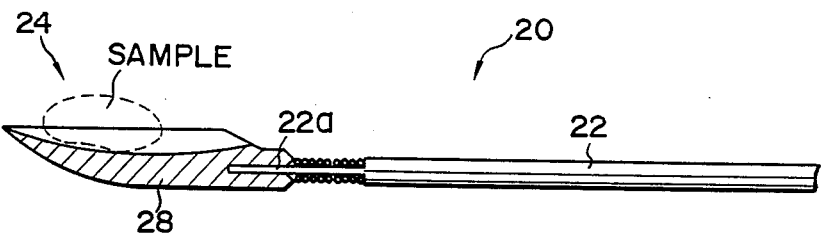
Figure 12:
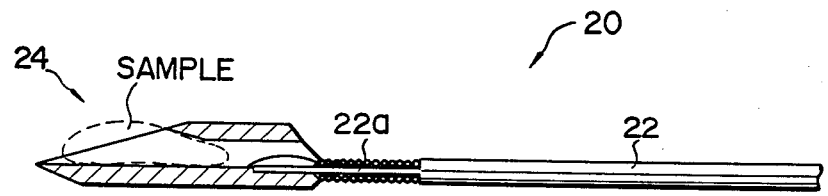
Figure 13:
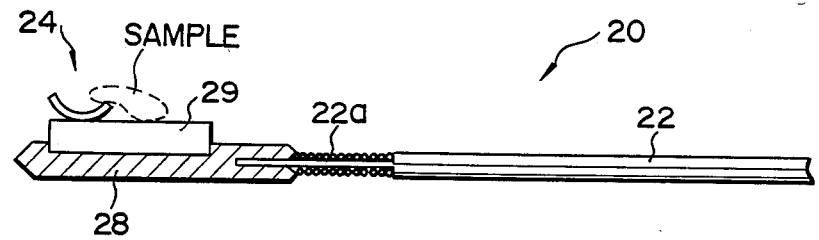

FIGS. 11 to 13 show guide means 20 of sixth to eighth variants. The guide means of these variants can pick up a sample from a rusty or dirty spot on the inner wall of a tubular channel or structure.

In the sixth variant shown in FIG. 11, slide member 24 of guide means 20 is formed as a spoon member having a sample pick-up recess at its upper surface and brazed to an arm member with reinforced wire 22a attached thereto. In the seventh variant shown in FIG. 12, guide means 20 is substantially the same as that of the sixth variant, but has slide member 24 formed of a diagonally-cut tubular member so that a sample can be kept thereon. Guide means 20 shown in FIG. 13 is comprised of base 28 fixed to arm member 22 with reinforced wire 22a attached thereto and magnet 29 fixed to the base. Guide means 20 of the eighth variant can withdraw a metal piece, etc., at the time of examination.

In the second to eighth variants, guide means 20 can be attached by attaching member 21 to rigid member 15 as in the first variant. As arm member 22 use is made of a single bar having proper rigidity and elasticity.

FIGS. 14 and 15 show ninth and tenth variants, respectively. In these variants, arm member 22 of guide means 20 has a length enough great as to extend from rigid section 15 to an operation section through insertion section 11. By withdrawing slide member 24 of guide means 20 the operator can get the visual field of the endoscope without obstruction at the time of observation.

In the ninth variant shown in FIG. 14, arm member 22 extends up to the operation section in a manner to be fixed by a plurality of holding rings or members 30 to insertion section 11.

Holding members 30 have insertion holes 31 for arm member 20 and are fixed to rigid section 11 and flexible section 13 with insertion holes 11 aligned along the axial direction of insertion section 11. A proper number of holding members enough adequate to support arm member 20 are provided as holding members 30. The holding member may be fitted into inner groove 32 so that it is prevented from being moved along the axial direction of insertion section 11. Arm member insertion holes 31 of holding member 30 may be formed as engaging grooves C-shaped in cross-section so that arm member 20 can be moved into and out of the engaging grooves. Furthermore, as arm member 20 use is made of not only the aforementioned flexible coil but also a single line having proper rigidity and elasticity.

In the ninth variant, the inner wall of the tubular channel or structure can be examined as in the first embodiment set forth above, but slide member 24 can be inserted into the pipe in an "withdrawn" state. In this variant, before rigid section 15 is to be inserted into the curve or bend of the tubular structure or channel, arm member 22 of the guide means is so operated that slide member 24 is brought to the near-center of the visual field of the operator. Then arm section 14 is bent and, controlling the extension length of arm member 22 and curvature of angle section 14, slide member 24 is brought past an abrupt step into abutting engagement with the inner surface of the tubular structure. Thereafter, the insertion section of the endoscope is further inserted through the guiding of rigid section 15 by guide means. In this way, the rigid section can successfully traverse the bend or curve of the channel structure.

FIG. 15 shows a tenth variant in which arm member 22 of guide means 20 extends into channel 33 of insertion section 11 of rigid section 15, angle section 14 and flexible section 12 up to operation section 12. Channel 33 may be an ordinary forceps insertion channel, not shown, or may be formed separate from the forceps insertion channel. In the latter case, channel 33 as indicated by a dot-dash line can be formed as a channel with the proximal end of operation section 12 closed.

Where arm member 22 of the guide means is to be inserted into channel 33, it is done through the ordinary forceps insertion hole, not shown, of the operation section with slide member 24 ahead and slide member 24 can be projected beyond the opening of rigid section 15 by pushing arm member 22. With channel 33 closed at the side of insertion section 12, arm member 22 is inserted through the opening of the rigid section 20 that slide member 24 is positioned near the rigid section 15. In the latter case, slide member 24 ca be made larger and be smoothly moved.

FIG. 16 shows an eleventh variant in which guide means is of a bellows type with a conical nose attached at the distal end so that compressed air can be supplied from hollow arm member 22 attached to, and opened into, the bellows-like slide member. Arm member 22 can be mounted as in ninth and tenth variants.

In the eleventh variant shown in FIG. 16, slide member 24 of guide means 20 normally occupies the position as indicated by a solid line in FIG. 16 and, upon being supplied with compressed air, expands into a shape as indicated by the dotted line in FIG. 16 so that it is given a firm tension.

Figure 17:
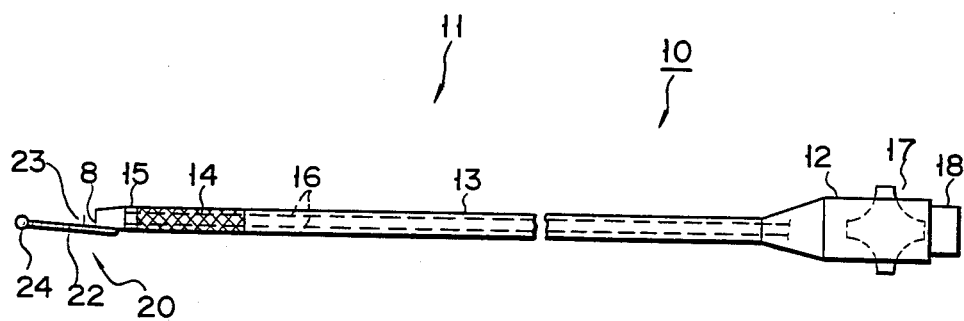
Figure 18:
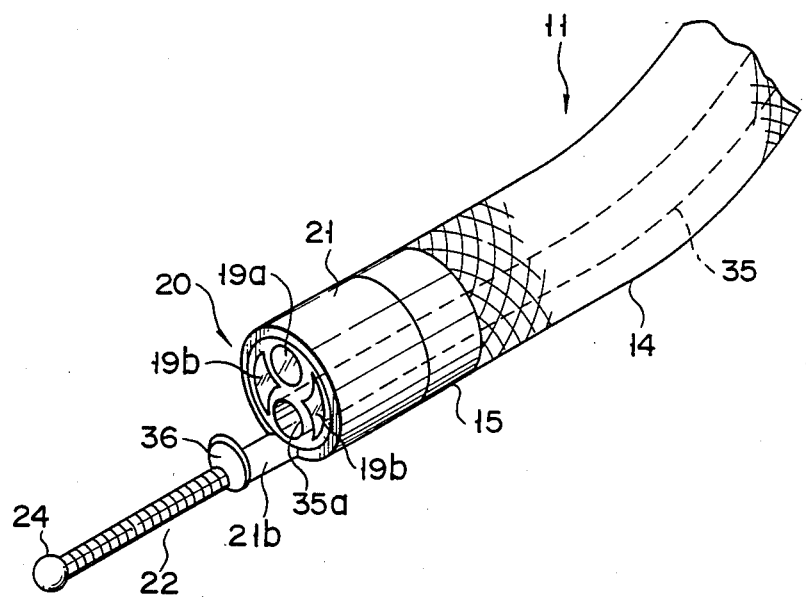

FIGS. 17 to 19 show an endoscope according to a second embodiment of this invention. In this second embodiment, it is possible to clean a fouling substance off the window of an optical system.

In FIGS. 17 to 19, similar reference numerals are employed to designate parts or elements corresponding to those shown in the first embodiment and first variant.

In the second embodiment shown in FIG. 17, guide means 20 has washing fluid guide 36. As seen from FIG. 18, tube 35 axially extends into insertion section 11 of the endoscope. At one end of tube 35, port 35a is formed which is opened at the distal end of rigid section 15. To the other end of tube 35, an air/liquid mechanism, not shown, is connected so as to supply a liquid, such as a washing liquid.

Guide means 20 which is attached to rigid section 15 has attaching member 21, as in the first variant (FIG. 6), comprised of a hollow metal cylinder with each end opened. To attaching member 21 is attached projection 21b which extends on the side opposite to that where rigid section 15 is located. Arm member 22 is attached to projection 21 and formed of a flexible coil. That is, arm member 22 of the guide means and slide member 24 attached thereto are attached by projecting 21b to attaching member 21.

In guide means 20 of this embodiment, washing liquid guide 36 is formed integral with projection 21b of attaching member 21. Washing liquid guide 36 is formed of a shallow pan whose reflection surface 37 faces port 35a of channel 35 when guide means 20 is attached to rigid section 15. Reflection surface 37 is formed as having a proper curvature, so that upon receiving a washing liquid injected from port 35a of channel 35 the reflection surface can splash the liquid back onto observation window 19a and illumination window 19b. Furthermore, washing liquid guide 36 is so located that it provides no substantial far to the visual field of observation window 19a and to the illumination light of illumination window 19b.

The second embodiment can be used in substantially the same way as the first embodiment explained in conjunction with FIG. 5, but it can also clean observation window 19a and illumination window 19b when they are soiled with a fouling substance.

That is, where observation window 19a and illumination window 19b are soiled with waste, rust, etc., deposited or formed on the inner wall of the pipe structure, the operator can view the soiled state through the eyepiece section and jet a washing liquid through channel 35 and port 55a so as to get a better visual field. Reflection surface 37 of the washing liquid guide causes the washing liquid which has been injected from port 35a to be vigorously splashed back onto observation window 19a and illumination window 19b so that these windows can be cleaned. It is, therefore, possible to get a better field of vision. In this case it has been proved more effective to, subsequent to jetting the washing liquid, jet air or gas through channel 35 and port 35 for drying.

In the aforementioned embodiment, an adapter (not shown) can be attached to rigid section 15, in place of guide means 20, in accordance with various uses to which the endoscope is put. Subsequent to removing guide means 20 from rigid section 15, a rod- or bar-like tool or instrument (no shown) can be inserted through channel 15 so that various operations can be performed.

FIG. 20 shows a first variant of the second embodiment.

In the first variant, cover glass 40 is mounted on the distal open end of attaching member 21. Projection 21b of the attaching member has, as a washing liquid guide, inlet chamber 38 communicating with channel 35 when attaching member 21 is to be attached to rigid section 15, and nozzle 39 which communicates with inlet chamber 38 and is directed toward cover glass 40. According to this variant, it is possible to prevent windows 19a, 19b of rigid section 15 from being injured by a hard foreign matter, etc., on the inner surface of the pipe structure. Cover glass 40 thus soiled can be washed clean by the washing liquid jetted from nozzle 39 via channel 35, port 35a and inlet chamber 38.

FIG. 21 shows a second variant of the second embodiment.

In the second variant, internal threaded section 41 is formed on the inner wall of port 35a of channel 35 and attaching member 21 for guide member 20 is comprised of a narrow cylinder which is inserted into port 35a which is opened into the free open end of rigid section 15. The base end portion of attaching member 21 has external threaded section 42 fitted into internal threaded section 41 an the free end of attaching member 21 is fixed to flexible coil-like arm member 22.

Attaching member 21 has inlet chamber 44 communicating with channel 35 when it is attached to rigid section 15 and nozzle 43 for guiding a washing liquid toward observation window 19a.

In this variant, guide means 20 is attached to rigid section 15 by threadably inserting member 21 into port 35a. This endoscope with the guide means attached thereto can be so formed as to have a narrow rigid section.

FIGS. 22 and 23 show endoscope 10 according to a third embodiment. The third embodiment is substantially the same as the aforementioned second embodiment in that windows 19a, 19b of the rigid section can be washed clean. In the third embodiment, however, a graduation mark is provided within a visual field with the diameter of a slide member of a guide means as a reference.

Guide means 20 as shown in FIG. 22 includes slide member 24 having a diameter D. Slide member 24, though shown as being spherical in shape, may have any other shape so long as it has a given proper shape and, at the same time, it can be slidably moved along the inner wall surface of the pipe. Within the operator's visual field 50 obtained through the optical system as shown in FIG. 23, graduation mark 51 with the outer diameter D of slide member 24 as a reference dimension L is shown located in a proper measurable position within substantially the same observation depth as that of slide member 24 without preventing the operator's observation Graduation mark 51 may be of such a type as to be formed with one half length (L/2) of the reference dimension L as a minimum unit as shown in FIG. 24. Graduation mark 51 is formed by a proper means, such as an etching step, on the inner surface of observation window 19a in units of an integral multiple of the reference dimension L. The graduation mark member may be any optical member so long as graduation mark 51 is formed in an optically conjugate position coupled by slide member 24 within an observation optical system or formed within an observable depth near to that position. Graduation mark 51 can be obtained with high measuring accuracy initially, taking into consideration the aberration of an optical image of the observation optical system. Mark 52 is formed within visual field 50 to allow the up-and-down direction to be identified thereby.

As shown in FIG. 23, endoscope 10 of the third embodiment has guide means 20, similar to that of the second embodiment, whereby rigid section 15 can effectively traverse step 4 formed between pipe 1 of a straight type and elbow 3 and can be washed clean effectively when windows 19a, 19b of the rigid section is soiled. Furthermore, endoscope 10 of the third embodiment is of such a type that the size of a region of interest (ROI), such as an injured spot 60, can readily be determined, while viewing the inner wall of the pipe through an eyepiece section of the operation section, with slide member 24 located near the spot 60 as shown in FIG. 23. In this case, the length of spot 60 located in substantially the same position as slide member 24 is compared with graduation mark 51 within visual field 50 as a reference. With the prior knowledge of the outer diameter D of slide member 24, the length of relatively great spot 60 can be instantly determined from graduation mark 51 because the outer diameter D of slide member 24 corresponds to the reference dimension L.

Where guide means 20 of FIG. 20 is used as the guide means of the third embodiment, a graduation is marked on cover glass 40 of attaching member 21. Furthermore, the third embodiment can be used as an ordinary endoscope or an adapter can be used in place of attaching member 21 in which case no graduation needs to be marked on the optical system of the endoscope.

This invention is not restricted to the aforementioned embodiments and obviously can be changed or modified without departing from the spirit and scope of this invention.

What is claimed is:

1. An endoscope comprising:
an elongated insertion section insertable into a channel;
an operation section connected to a base end of said insertion section, and adapted to control the insertion section from outside of said channel;
said operation section having an eyepiece section and said insertion section including a flexible section connected at its base end to said operation section and having a remote end, an angle section connected at its base end to the remote end of said flexible section, having a remote end and adapted to have its curvature controlled by the operation of said operation section, and a rigid section connected at its base end to the remote end of said angle section, having a remote end and having an observation window capable of observing an inner wall of said channel space; and guide means mounted on said rigid section and capable of guiding said rigid section along an inner wall of said channel, and around a curve or bend thereof;

wherein said guide means includes an elongated arm member extending substantially in an axial direction of said rigid section, and having proper rigidity and elasticity, said arm member being fixed at its first end to said rigid section and having a distal-side remote end, and said guide means further includes a slide means fixed to the second end of said arm member and slidable along the inner surface of said channel space.

2. An endoscope according to claim 1, further including an optical system for optically connecting said eyepiece section to said observation window, and wherein said arm member is of such a type that said second end thereof extends toward the middle of an operator's visual field obtained through said eyepiece section, and said slide member is located within said visual field such that it is situated at a level lower than a middle level of said visual field.

3. An endoscope according to claim 2, wherein said rigid section has a stepped-cylindrical shape having a small- and a large-diameter section, an external threaded section is formed at least partially on the small-diameter section of said rigid section, said guide member has an attaching member to which said first end of said arm member is fixed, and said attaching member has a hollow-cylindrical configuration open at each end in the axial direction and internal threaded section over which said external threaded section of said rigid section is inserted.

4. An endoscope according to claim 2, wherein said first end of said arm member is fixed directly to an outer periphery of said rigid section.

5. An endoscope according to claim 2, wherein said guide means has a holding ring fixed at least to said rigid section, said holding ring has a projection capable of fixing said first end of said arm member to said rigid section, in parallel fashion, and said first end of said arm section has an extension leading to said operation section, along said insertion section.

6. An endoscope according to claim 5, wherein said guide means has a plurality of holding rings fixed to said rigid section and said flexible section, and each having a projection aligned along the axial direction of said insertion section, to allow said extension to be moved along the axial direction thereof.

7. An endoscope according to claim 6, wherein the projections of said holding rings each have a through-hole aligned along said axial direction of said insertion section and into which said arm member is inserted.

8. An endoscope according to claim 6, wherein said projections of said holding rings each have an engaging groove C-shaped in cross-section, the engaging grooves being aligned with each other along the axial direction of said insertion direction.

9. An endoscope according to claim 1, wherein said insertion section has a channel externally opened at a location of said rigid section and leading to said operation section, said first end of said arm member having an extension leading from said rigid section to said operation section, and said extension being held within and along said channel.

10. An endoscope according to claim 9, wherein said channel is closed at the side of said insertion section.

11. An endoscope according to claim 3, wherein said insertion section has a washing liquid flow tube extending therein and is externally opened at said rigid section, and said guide means has a washing liquid guide located at a position where an operator has a clear field of view, said washing liquid guide being of such a type that, upon receiving said washing liquid injected via said washing liquid flow tube, it is vigorously splashed back onto said observation window.

12. An endoscope according to claim 11, wherein said attaching member has a projection for fixing said arm member in place, and said projection has said washing liquid guide.

13. An endoscope according to claim 12, wherein said washing liquid guide is of such a pan-like type that its face opposite to said rigid section, upon receiving said washing liquid via said washing liquid flow tube, can splash it back onto said observation window.

14. An endoscope according to claim 12, wherein said attaching member has a glass cover for covering an opening on the side of said projection, and said projection of said attaching member has an inlet chamber leading to said tube, when said attaching member is attached to said rigid section, and a nozzle communicating with an inlet chamber and directed toward said glass cover, said input chamber and said nozzle constituting said washing liquid guide.

15. An endoscope according to claim 2, wherein said insertion section has a washing liquid flow tube therein externally opened at said rigid section, said guide means is connected at one end to a first end of said arm member and has the other end which has a narrow cylindrical attaching member threadably insertable into a port of said rigid section, and said narrow cylindrical attaching member has an internal chamber leading to said tube when said attaching member is attached to said rigid section, and a nozzle communicating with said internal chamber and directed toward said observation window.

16. An endoscope according to claim 2, wherein a graduation mark having said slide member as a reference is arranged within said optical system such that it is formed within nearly the same observation depth as that of said slide member.

17. An endoscope according to claim 16, wherein said graduation mark is formed within said observation window.

18. An endoscope according to claim 14, wherein a graduation mark having said slide member as a reference is provided at said cover glass such that it is formed within nearly the same observation depth as that of said slide member.

19. An endoscope according to claim 6, wherein said arm member is formed of an elongated hollow pipe for supplying compressed air or gas, and said slide member is formed of a bellows expandable by the compressed air or gas which is supplied via said hollow pipe.

20. An endoscope according to claim 5, wherein said slide member is formed as a metal ball.

21. An endoscope according to claim 5, wherein said slide member is formed as a brush or the like.

22. An endoscope according to claim 5, wherein said slide member is so formed that it can pick up a sample.

23. An endoscope according to claim 5, wherein said slide member is formed of a rigid plastic such that it has a bulb-like configuration.

* * * * *